(12) United States Patent
Riss et al.

(10) Patent No.: US 8,461,385 B2
(45) Date of Patent: Jun. 11, 2013

(54) MANUFACTURE PROCESS OF ORGANIC COMPOUNDS

(75) Inventors: Bernhard Riss, Huningue (FR); Ulrich Meier, Riehen (CH)

(73) Assignee: Novartis AG, Basel (CH)

( * ) Notice: Subject to any disclaimer, the term of this patent is extended or adjusted under 35 U.S.C. 154(b) by 1127 days.

(21) Appl. No.: 11/721,817

(22) PCT Filed: Dec. 14, 2005

(86) PCT No.: PCT/EP2005/013454
§ 371 (c)(1),
(2), (4) Date: Jun. 15, 2007

(87) PCT Pub. No.: WO2006/063821
PCT Pub. Date: Jun. 22, 2006

(65) Prior Publication Data
US 2009/0253811 A1    Oct. 8, 2009

(30) Foreign Application Priority Data

Dec. 16, 2004  (GB) .................................. 0427603.6

(51) Int. Cl.
*C07C 233/65*    (2006.01)

(52) U.S. Cl.
USPC .............................................. 564/177; 544/94

(58) Field of Classification Search
USPC .............................................. 564/177; 544/94
See application file for complete search history.

(56) References Cited

U.S. PATENT DOCUMENTS

| 7,420,085 B2 * | 9/2008 | Bhandarkar et al. ........... 562/450 |
| 7,495,030 B2 * | 2/2009 | Gschneidner .................. 514/557 |
| 2002/0065255 A1 | 5/2002 | Bay et al. ...................... 514/166 |
| 2002/0123459 A1 | 9/2002 | Ault et al. ......................... 514/2 |
| 2003/0216593 A1 | 11/2003 | Bay et al. ...................... 560/143 |
| 2005/0054557 A1 | 3/2005 | Goldberg ........................... 514/2 |
| 2005/0148497 A1 | 7/2005 | Khan ................................ 514/8 |

FOREIGN PATENT DOCUMENTS

| WO | 00/59863 | 10/2000 |
| WO | WO 01/70219 | 9/2001 |

* cited by examiner

*Primary Examiner* — Shailendra Kumar
(74) *Attorney, Agent, or Firm* — Ann R. Pokalsky, Esq.; Dilworth & Barrese, LLP

(57) ABSTRACT

The present invention relates to a method of preparing N-substituted salicylamides or derivatives thereof, and their salts, hydrates and solvates. In particular, the present invention relates to a method of preparing N-(5-chlorosalicyloyl)-8-aminocaprylic acid (5-CNAC) and its corresponding disodium monohydrate.

56 Claims, No Drawings

MANUFACTURE PROCESS OF ORGANIC COMPOUNDS

This application is a 371 of PCT/EP2005/013454, filed 12/14/2005.

The present invention relates to a method of preparing N-substituted salicylamides or derivatives thereof, and their salts, hydrates and solvates. In particular, the present invention relates to a method of preparing N-(5-chlorosalicyloyl)-8-aminocaprylic acid (5-CNAC) and its corresponding disodium monohydrate.

The N-substituted salicylamides as prepared by the method of the present invention are suitable for use in compositions for delivering active agents via oral or other routes of administration to mammals.

BACKGROUND TO INVENTION

Processes for preparing N-substituted salicylamides are disclosed in, for example, WO00/59863, WO01/92206 and WO01/70219, and an example process for preparing 5-CNAC (an N-substituted salicylamide) that is known in the art is shown in Scheme 1.

In addition, a common method of producing the salt of the 5-CNAC in the presence of NaOH and acetone is as shown in Scheme 2.

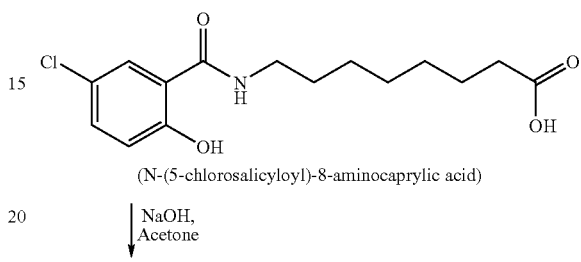

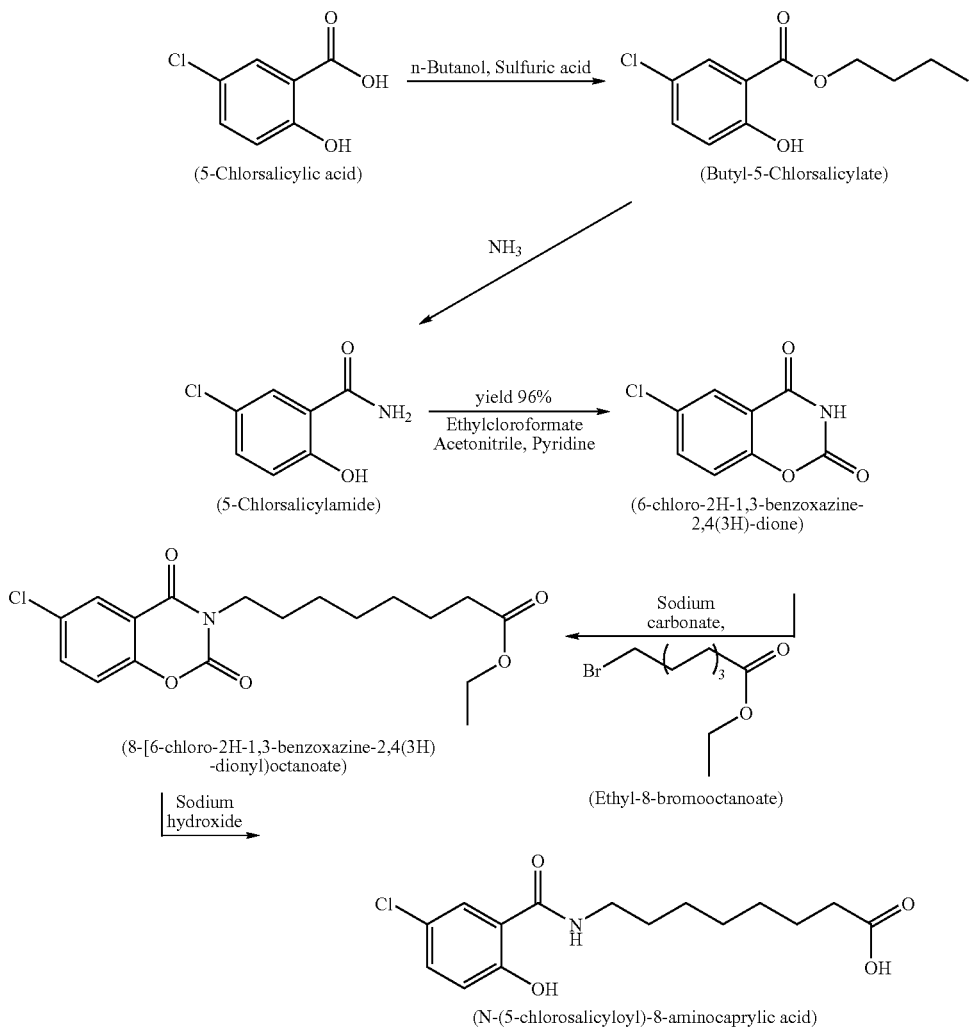

-continued

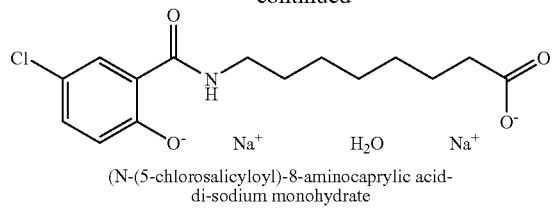

(N-(5-chlorosalicyloyl)-8-aminocaprylic acid-
di-sodium monohydrate)

The present invention seeks improve the process of the prior art with a view to achieving a robust high yielding process suitable for producing bulk quantities of high quality product.

SUMMARY OF THE INVENTION

In a broad sense, the present invention relates to a method of preparing N-substituted salicylamides or derivatives thereof and their salts. The method comprises reacting a chloro-substituted compound of formula (III) (as defined below) with carsalam (6-chloro-2H-1,3-benzoxazine-2,4 (3H)-dione) or a derivative thereof, as required, in the presence of a source of bromide ions, for example an alkali metal bromine salt, e.g. NaBr.

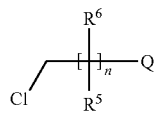
(III)

wherein n is and integer from 1 to 8, Q represents a group readily convertible to a carboxylic acid moiety and $R^5$ and $R^6$ are independently selected from hydrogen, —OH, $NR^3R^4$, halogen, $C_1, C_2, C_3$ or $C_4$ alkyl, $C_1, C_2, C_3$ or $C_4$ alkoxy, $C_2, C_3$ or $C_4$ alkenyl where $R^3$ and $R^4$ are each independently selected from hydrogen, —OH, $C_1, C_2, C_3$ or $C_4$ alkyl, $C_1, C_2, C_3$ or $C_4$ haloalkyl, $C_1, C_2, C_3$ or $C_4$ alkoxy, $C_2, C_3$ or $C_4$ alkenyl.

A preferred class of compounds of formula III have the formula III.II as shown below:

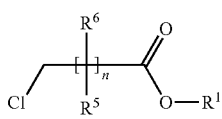
(III.II)

The presence of the alkali metal bromine salt (preferably NaBr) is believed to allow the formation of the bromo-substituted compound of formula (IIIb)

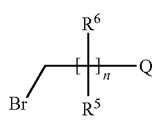
(IIIb)

Furthermore, the aforementioned method of the present invention provides a method of preparing an N-substituted salicylamide of formula (IV) and, by means of, for example, an acid workup, its corresponding free carboxylic acid (IV.II).

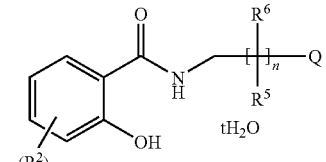
(IV)

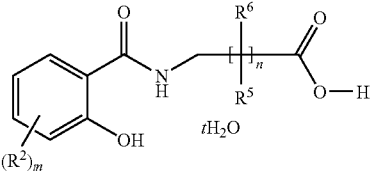
(IV.II)

where t is 0, 1, 2, 3, 4, 5 or 6, m is 1, 2, 3 or 4 and $R^2$, or where m>1, each $R^2$ independently, is selected from —OH, $NR^3R^4$, halogen, $C_1, C_2, C_3$ or $C_4$ alkyl, $C_1, C_2, C_3$ or $C_4$ haloalkyl, $C_1, C_2, C_3$ or $C_4$ alkoxy, $C_2, C_3$ or $C_4$ alkenyl and $R^3$ and $R^4$ are each independently selected from hydrogen, —OH, $C_1, C_2, C_3$ or $C_4$ alkyl, $C_1, C_2, C_3$ or $C_4$ haloalkyl, $C_1, C_2, C_3$ or $C_4$ alkoxy, $C_2, C_3$ or $C_4$ alkenyl.

In another aspect of the Invention, the alkali metal salt (V) of the N-substituted salicylamide is prepared in the presence of an aqueous solution of the alkali metal cation, $M_a^+$, for example Na+, in an acetone/water mixture. Other suitable mixture are any water miscible solvents, such as acetone/water, ethanol/water or acetonitrile/water.

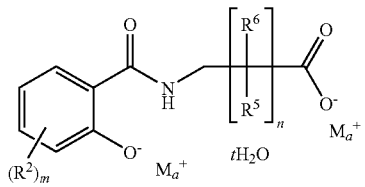
(V)

More specifically, the method of the present invention employs a chloro substituted compound of formula (III.II) (as defined below), and especially a chloro-substituted ester. In particular, the present invention relates to a method of preparing (N-(5-chlorosalicyloyl)-8-aminocaprylic acid (5-CNAC) and its corresponding salts, especially the disodium monohydrate. In a preferred embodiment, the method comprises reacting an alkyl chloro octanoate, especially ethyl chlorooctanoate (ECO), with 6-chloro-carasalam in the presence of NaBr to form 5-CNAC. The disodium monohydrate salt is subsequently formed by reacting the 5-CNAC with NaOH in an acetone/water mixture.

The N-substituted salicylamides, especially 5-CNAC, as prepared by the method of the present invention are suitable for use in compositions for delivering active agents via oral or other routes of administration to mammals. In particular, the compounds prepared for the present invention may be used for the delivering of pharmaceutically, physiologically, pharmacologically, radiologically or other active agents to a target in the body of a warm blooded animal.

DETAILED DESCRIPTION OF THE PRESENT INVENTION

A general reaction sequence according to the invention is shown in Scheme 3. In Scheme 3 there is shown a method of preparing N-substituted salicylamides or derivatives thereof (IV) and their salts (V) from the corresponding salicylamide (I), via the corresponding carsalam derivative (II) in the presence of the chloro-substituted compound (III):

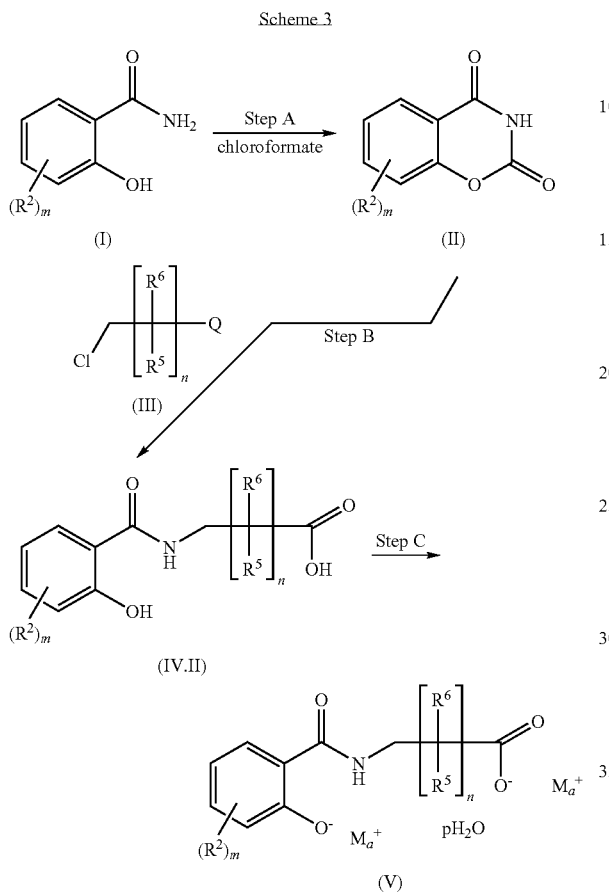

In reaction Scheme 3:

t is 0, 1, 2, 3, 4, 5 or 6 and preferably t is 0; p is preferably 0, 1, 2, 3, 4, 5, or 6 and preferably p is 1. The hydrates $tH_2O$ and $pH_2O$ shown in Scheme 3 may alternatively be a solvate, a mixed hydrate and solvate or a mixed solvate.

n is and integer from 1 to 8 and preferably n is 6; m is 1, 2, 3 or 4 and preferably m is 1.

M is an alkali metal preferably $M_a$ is Na or K. Most preferably, the alkali metal M is Na (and therefore $M_a^+$ is $Na^+$). M may be present in the form $M_aY$, where Y is a basic counter-ion, e.g. carbonate or hydroxide. Particularly preferably $M_aY$ is NaOH.

Q represents a group readily convertible to the carboxylic acid moiety of formula (IV.II). For example, Q may represent a protected carboxylic acid group, the protecting group being removeable, preferably in a final work-up stage in Step B. Thus Q is a moiety which does not participate in the reaction with the compound of formula (III) in Step B, but is subsequently readily convertible into the free carboxylic acid, such as in acid work-up conditions.

$R^2$— or where m>1, each $R^2$ independently—may be selected from —OH, $NR^3R^4$, halogen, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, $C_2$, $C_3$ or $C_4$ alkenyl.

$R^3$ and $R^4$ are each independently selected from hydrogen, —OH, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, $C_2$, $C_3$ or $C_4$ alkenyl.

The respective $R^5$ and $R^6$ moieties are independently selected from hydrogen, —OH, $NR^3R^4$, halogen, $C_1$, $C_2$, $C_3$ or $C_4$ alkyl, $C_1$, $C_2$, $C_3$ or $C_4$ alkoxy, $C_2$, $C_3$ or $C_4$ alkenyl. The respective $R^5$ moieties may or may not be the same and likewise the respective $Rr^5$ moieties may be the same or different. Similarly the respective $R^5$ and $R^6$ moieties may be the same or different. In a preferred embodiment every $R^5$ and every $R^6$ is hydrogen.

Halogen may be selected from chloro, fluoro, bromo and iodo. Most preferred is chloro.

It is preferred that m is 1 and that $R^2$ is halo. Preferably $R^2$ is chloro. It is still further preferred that when m is 1, $R^2$ is at the 5-position.

Step B may comprise one or more sub-steps in which intermediate compounds are formed but are most preferably not isolated. Such intermediates may include those identified below as compounds of formulae (IV.I) and (VI).

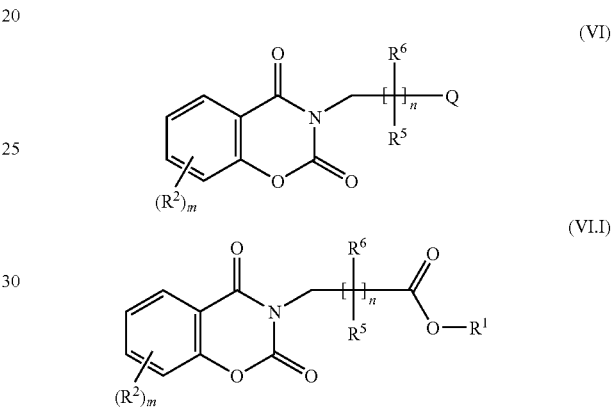

The present invention may therefore provide an additional step of saponifying the reaction mixture containing (IV) to further react the intermediate having the formula (VI) to form the target molecule. This step may be carried out without the need to isolate either of the compounds of formula IV or VI.

Most preferably the compound of formula (III) is comprises a compound of formula (III.II) below:

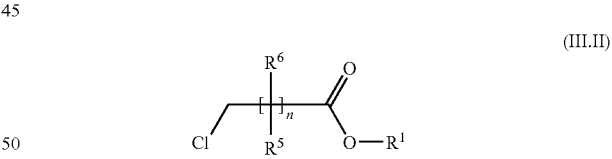

in formula (III.II), in general terms, $R^1$ may be a protecting group for the carboxy moiety, more especially a group which is substantially inert to reaction with —$NH_2$ groups during step A but convertible thereafter to a carboxylic acid (—COOH) group. It is especially preferred that $R^1$ is selected from a linear or branched alkyl group containing 1, 2, 3, 4, 5 or 6 carbon atoms, preferably 1, 2, 3 or 4 carbon atoms and particularly 1 or 2 carbon atoms, so that formula (III.II) represents an ester. In a particularly preferred embodiment, $R^1$ is ethyl ($C_2$). Thus the compound of formula (III.II) is most preferably an ester.

A preferred compound of formula (III) and (III.II) is where n is 6 and each $CR^5R^6$ is $CH_2$, thus comprising a linear hexyl chain. One preferred compound comprises ethyl-8-chlorooctanoate (III.II):

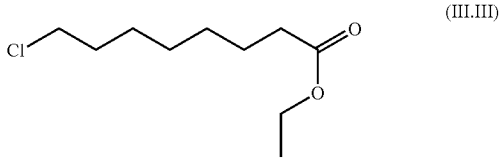 (III.III)

A preferred class of compounds formed in the method of the invention having the general formula IV may be exemplified by the formula IV.I below:

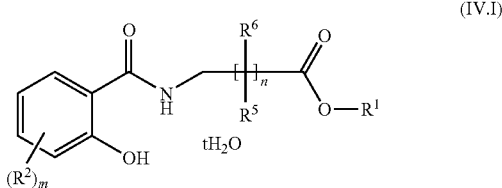 (IV.I)

where R1 is a protecting group for the carboxy moiety. Such compounds are preferably intermediates which are not isolated.

In compounds shown herein, such as those of formulae (I) and (IV), which include a phenolic hydroxy group, the said group may be in the form of a salt, for example a sodium salt.

The phenolic hydroxy group may be present in the deprotonated form during reaction steps A and B, where the presence of a base is required.

Reagents

The following discussion relates to the reagents that are preferably used in the present invention. Particular reaction conditions are discussed in a later section.

Step A

In Step A, the salicylamide (I) is converted into the corresponding carsalam derivative (II) by reaction with an excess of a chloroformate such as ethylchloroformate, n-propylchloroformate, i-propylchloroformate, n-butylchloroformate or t-butylchloroformate. Ethylchloroformate is particularly preferred. The reaction is preferably carried out in a two-phase system of an alkyl acetate/mild organic base/water. Preferably the mild organic base is substantially water insoluble.

Examples of an alkyl acetate are methyl acetate, ethyl acetate, n-propyl acetate, i-propyl acetate, t-butyl acetate. Most preferably the reaction is carried out in n-butyl acetate.

Examples of a mild organic base are pyridine and a pyridine derivative in particular an alkyl substituted pyridine, for example a dialkylsubstituted pyridine, and more especially those pyridine derivatives which are substantially water insoluble. An example of a preferred pyridine derivative is 5-ethyl-2-methyl-pyridine.

Particularly preferably, the reaction is carried out in the two-phase system comprising n-butyl acetate/5-ethyl-2-methyl-pyridine/water in an excess (e.g. 20% excess) of ethylchloroformate. Most preferably, the acetate:water ratio is about 1:1.

Step B

Step B Preferably Comprises a Series of Sub-Steps:

Step B1

Step B1 is the primary reaction step in which the carsalam or carsalam derivative of formula (II) reacts with the chloro-substituted compound (III). Preferably the chloro-substituted compound (III) is an ester and the reaction is carried out in the presence of a base, such as sodium carbonate, and an aprotic solvent such as a dialkylamide, for example dimethylacetamide or dimethylformamide. Reaction in the presence of dimethylformamide is preferred. In addition a source of bromide ions, for example a catalytic amount of the alkali metal-bromide MBr, for example KBr or NaBr, especially NaBr is present.

The aprotic solvents suitable for use in this invention may include, but are not limited to, the following: nitrile compounds (e.g., acetonitrile, benzonitrile, nitromethane), amide and cyclic amide compounds (e.g., N,N-dimethylformamide, N-methylformamide, N,N-diethylformamide, N-ethylformamide, N,N-dimethylacetamide, N-methyl-2-pyrrolidone,-hide), ester, cyclic ester, and ether compounds (e.g., tetrahydrofuran, propylene carbonate, ethylene carbonate, gamma-butyrolactone, ethyl acetate, dimethylether), oxide and sulfo compounds (e.g., dimethylsulfoxide, acetone, sulfolane, dimethylsulfone).

Preferably, the aprotic solvent is an amide selected from N,N-dimethylformamide, N-methylformamide, N,N-diethylformamide, N-ethylformamide, N,N-dimethylacetamide. Most preferably, the solvent is N,N-dimethylformamide.

Step B2

In a second part of step B, an alkali metal salt, for example sodium hydroxide is added to the reaction mixture together with water.

Step B3

In a third part of step B an acid is added, for example sulfuric acid together with an alkyl acetate for example methyl acetate, ethyl acetate, n-propyl acetate, i-propyl acetate, t-butyl acetate. Most preferably the third part of step B is in the presence of ethyl acetate. Step B3 forms the free acid of formula (IV.II).

Step B4

In a preferred fourth part of Step B, the N-substituted salicylamide (IV.II) is crystallised in an alcohol, for example ethanol/water, however other solvent might be suitable too, especially mixture of ethyl acetate, ethanol, water, or acetone/water.

Step C

In step C the N-substituted salicylamide of formula (IV.II) is reacted with a strong base, for example sodium hydroxide, in the presence of acetone and water.

The processes of this invention, where carried out in the presence of a strong base, for example, $M_aY$, may be carried out in the presence of alkali metal or alkaline earth metal hydroxides, hydrides, amides, alkanolates, phenolates, acetates, carbonates, dialkylamides or alkylsilyl-amides; alkylamines, alkylenediamines, optionally N-alkylated, optionally unsaturated, cyclo-alkylamines, basic heterocycles, ammonium hydroxides, as well as carbocyclic amines.

Alkyl-alkali metals may be selected from, for example, methyllithium, n-butyllithium, or tertbutyllithium optionally activated with tetramethylethylene diamine (TMEDA).

Alkali metal hydrides, may be selected from, for example, sodium hydride and calcium hydride.

Alkali metal amides may be selected from, for example, lithium amide or lithium diisopropylamide (LDA), lithium diethylamide, lithium isopropylcyclohexylamide or potassium bis(trimethylsilyl)amide.

Alkali metal alcoholates or alkali metal alcoholates may be selected from, for example, primary, secondary or tertiary aliphatic alcohols containing 1 to 10 carbon atoms, e.g. sodium, potassium or lithium methylate, sodium, potassium or lithium ethylate, sodium, potassium or lithium n-propylate, sodium potassium or lithium isopropylate, sodium, potassium or lithium n-butylate, sodium, potassium or lithium sec-butylate, sodium, potassium or lithium tert-butylate, sodium potassium or lithium 2-methyl-2-butylate, sodium, potassium or lithium 2-methyl-2-pentylate, sodium, potassium or lithium 3-methyl-3-pentylate, sodium potassium or lithium 3-ethyl-3-pentlyate.

Alkaline earth metal phenolates may be selected from, for example, alkaline metal o-alkyl substituted phenolates, alkali metal phenolates or alkali metal o-alkyl substituted phenolates, e.g. sodium or potassium o-cresolate.

Amine-based organic bases also may be used and may be selected from, for example, 2,4,6-Trimethylpyridine; 2-tert-Butyl-1,1,3,3-tetramethyl-guanidine; 1,8-Diazabicyclo[5.4.0]undec-7-ene (DBU); 2,3,4,6,7,8,9,10-Octahydropyrimidol[1,2-a]azepine; 1,5-Diazabicyclo[4.3.0]non-5-ene (DBN); diazabicyclooctane (DABCO); 1,4-Diazabicyclo(2.2.2)octane (TED); N,N-Dicyclohexylmethylamine; N,N-Diethylaniline; N,N-Diisopropyl-2-ethylbutylamine; N,N-Diisopropylmethylamine; N,N-Diisopropyl-3-pentylamine; N,N-Dimethylaniline; 2,6-Di-tert-butyl-4-methylpyridine; N,N-Diisopropylethylamine; 2,6-Dimethylpyridine; 7-Methyl-1,5,7-triazabicyclo(4.4.0)dec-5-ene (MTBD); 3,3,6,9,9-Pentamethyl-2,10-diazabicyclo-(4.4.0)dec-1-ene (PMDBD); 1,2,2,6,6-Pentamethylpiperidine (PMP); Triethylamine; 1,1,3,3-Tetramethylguanidine (TMG); N,N,N',N'-Tetramethyl-1,8-naphthalenediamine; 2,2,6,6-Tetramethylpiperidine (TMP); 1,5,7-Triazabicyclo(4.4.0)dec-5-ene, 1,3,4,6,7,8-Hexahydro-2H-pyrimido[1,2-a]pyrimidine (TBD); Tributylamine; 2,4,6-Tri-tert-butylpyridine; Tris(trimethylsilyl)amine; and alkyl-ammonium hydroxides.

However, a mixture of the above bases may also be employed.

Those which may be mentioned by way of example are sodium hydroxide, hydride, amide, methanolate, acetate, carbonate, potassium tert.-butanolate, hydroxide, carbonate, hydride, lithium diisopropylamide, potassium bis(trimethylsilyl)-amide, calcium hydride, triethylamine, diisopropylethylamine, triethylenediamine, cyclohexylamine, N-cyclohexyl-N,N-dimethyl-amine, N,N-diethylaniline, pyridine, 4-(N,N-dimethylamino)pyridine, quinuclidine, N-methylmorpholine, benzyltrimethylammonium, as well as 1,5-diazabicyclo[5.4.0]undec-5-ene (DBU).

In the processes of this invention the preferred bases are alkali metal hydroxides and carbonates, for example sodium hydroxide and sodium carbonate.

In preferred reaction conditions of step C, the acetone:water ratio is about 3:1, which may be increased up to 4:1, or even about 5:1 up to a highest level of about 15:1, during the reaction by addition of further acetone to the reaction mixture.

It will be understood that in between addition of reagents and in particularly in between steps A, B or C, or indeed between the various parts of step B, evaporation, filtration, extraction and other final and/or preparatory steps may be conducted prior to commencing the next step.

Conditions

Unless stated to the contrary, the reaction steps of the present invention are most preferably conducted in an inert atmosphere, for example under a nitrogen atmosphere.

Step A

In step A, the reaction mixture is cooled to 0-5° C. during the addition of the chloroformate and the mixture is then slowly heated to reflux temperature and refluxed until the reaction has reached a sufficient degree of completion. Typically the reaction mixture is refluxed for about 3 to 7 hours, and more especially for about 5 hours. The temperature of the reflux is dependent upon the alkyl acetate solvent present. A typical reflux temperature is in the range of 80 to 120° C.

Step B

In step B1, after addition of all the components of the reaction mixture except the sodium carbonate, the reaction mixture is heated to about 100° C. The addition of sodium carbonate then preferably takes place over about two hours.

In step B2, the reaction mixture of is heated to about 100° C.

In step B3, the reaction mixture is cooled to about 60° C. prior to the addition of the acid. Preferably a temperature of about 60° C. is maintained throughout the reaction and this temperature is preferably maintained throughout any subsequent purification steps, for example extractions.

In step B4, the alcohol (preferably ethanol) is added at about 50-60° C. and then the solution cooled to about 40-50° C. Finally, the solution is cooled to about 0-5° C.

In preferred embodiments, the present invention relates to a method of preparing N-(5-chlorosalicyloyl)-8-aminocaprylic acid (5-CNAC) and its corresponding salts, in particular its disodium monohydrate. In one particularly preferred embodiment, 5-CNAC is prepared from 5-chlorosalicyclic acid via 5-chloro carsalam, in the presence of ethyl-8 chlorooctanoate (ECO) as shown in Scheme 4 below:

Scheme 4

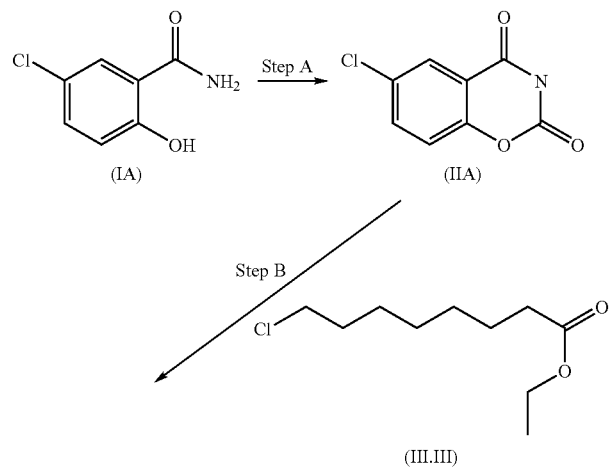

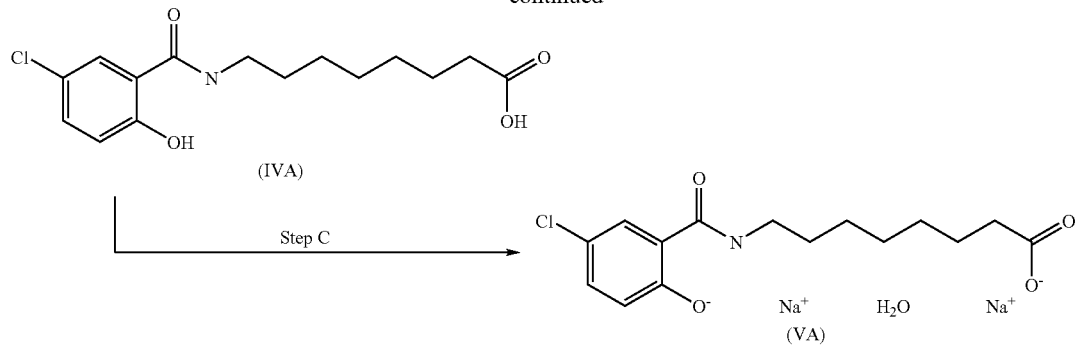

The reagents for steps A, B and C are as hereinbefore described in Scheme 3.

The most preferred reagents for processes described in the present invention, in particular for the process of Scheme 4 are as follows:

In step A, the 5-chloro-salicylamide is reacted with ethyl-chloroformate (excess) in an n-butyl acetate/water mixture, with 5-ethyl-2-methyl-pyridine acting as the required organic base.

In step B1 the 5-chloro-carsalam is reacted with ethylchlorooctanoate in the presence of a sodium carbonate and NaBr (bromide ion source) in dimethylformamide. NaBr is believed to act catalytically. In step B2, the resulting product is treated with, for example aqueous sodium hydroxide. Then, an acid, preferably a mineral acid such as sulfuric acid, is added followed by ethyl acetate. The crude product is recrystallised in ethanol.

In step C the 5-CNAC is treated with sodium hydroxide in an acetone/water mixture, preferably at a ratio of acetone:water of 3:1.

A second aspect of the present invention, relates to the use of the N-substituted salicylamides and derivatives thereof, in particular 5-CNAC, and their corresponding salts, in particular their disodium monohydrate salts, when prepared by the method of the present invention, for delivering active agents, such as biologically or chemically active agents, to a target.

A third aspect of the present invention relates to pharmaceutical compositions of the N-substituted salicylamides and derivatives thereof and salts thereof when prepared by the method of the present invention. In particular the present invention relates to pharmaceutical compositions comprising 5-CNAC when the 5-CNAC is prepared by the method of the present invention The disclosure hereinafter discusses the merits of the present invention primarily in terms of the synthesis of 5-CNAC. However, it will be appreciated that the discussion of the invention in these terms is not intended to limit the scope of the invention, which extends to the N-substituted salicylamides of general formula IV. Thus the following discussion of the synthesis in terms of 5-CNAC merely represents a preferred embodiment of the present invention which conveniently allows for comparisons between the present invention and the prior art. The skilled man will appreciate that the process of the present invention is not limited only to the synthesis of 5-CNAC.

A preferred synthesis of the present invention provides an improved procedure for obtaining 5-CNAC as compared to the prior art. It will be recalled that the prior art, as described in Scheme 1, is a process in which the formation of 5-CNAC is achieved by reaction with ethyl-8 bromooctanoate in the presence of sodium carbonate and dimethylacetamide.

The synthesis of 5-CNAC of the present invention advantageously uses 5-chlorosalicylamide as a newly available starting material instead of 5-chlorosalicylic acid in the prior art, thus avoiding currently present in the prior art.

The present invention also provides a new procedure for the synthesis of 6-chlorocarsalam, a key intermediate in the process for the manufacture of 5-CNAC, in which a two-phase mixture (for example n-butyl acetate/water) with an alkyl substituted pyridine, for example a dialkylsubstituted pyridine such as 5-ethyl-2-methyl-pyridine as the base is used. The use of pyridine as the mild organic base is not precluded in the present invention, although it is not preferred. One particular advantage of using certain pyridine derivatives, e.g. 5-ethyl-2-methyl-pyridine, instead of pyridine in the prior art is that the former is recoverable under these conditions. In comparison, the prior art process uses a reaction mixture consisting of ethylchloroformate in acetonitrile, with pyridine as the base, none being reported as recoverable.

The process of the present invention also achieves a major advantage over the prior art by the use of the two-phase system. This system enables the hydrolysis of unwanted intermediates caused by side reactions, which in turn removes them from the reaction mixture and as a result provides a much purer final product.

In a preferred synthesis of 5-CNAC from the previously prepared 6-chlorocarsalam according to the method of the present invention, ethyl-8-chlorooctonoate (ECO) is reacted with 6-chloro-carsalam in the presence of dimethylformamide and sodium carbonate (acting as the base) together with an amount of sodium bromide. These conditions are believed by the inventors to allow the formation of the more reactive ethyl-8-bromooctonoate (EBO) In situ. Sodium bromide can be recovered at the end of the reaction and in at least this sense the sodium bromide is believed to act catalytically. Therefore the process of the present invention has removed the need to use ethyl-8-bromooctonoate (EBO) directly as a starting material. EBO has known health and environmental concerns due to its highly reactive characteristics. Furthermore, ECO is cheaper and more readily available than EBO.

The intermediate ester (or esters) formed by the aforementioned reaction is (are) most preferably not isolated but saponified immediately after concentration of the end reaction mixture. This saponification is advantageous in eliminating the necessity of isolation of the product, thereby increasing the likelihood of obtaining a higher yield. This can be contrasted with the corresponding stage of the prior art which required the isolation of 8-[6-chloro-2H-1,3-benzoxazine-2, 4(3H)dionyl]octanoate. The highly pure free acid is then obtained by extraction and crystallisation.

Finally, the formation of the disodium monohydrate is formed (Step C) by the addition of sodium hydroxide in an acetone/water mixture advantageously allows a crystallisation from a homogenous solution, in contrast to the emulsion of the prior art where sodium hydroxide is added to pure acetone. The homogeneous solution allows large crystals to be obtained which might be dried on a standard rotary paddle.

As a result of the changes implemented by the present invention (as exemplified for the above process for the synthesis of 5-CNAC), a new process has been developed that provides N-substituted salicylamides of formula IV, especially 5-CNAC (IVA), in both a cost-effective manner and at high purity.

The process of the present invention, using the synthesis of 5-CNAC as an example, is described below in further detail, with particular reference to Schemes 5 and 6 below:

Step A

The temperature T as illustrated in Scheme 5 is preferably in the range of 80-120° C. Most preferably the temperature T is between 85-95° C. Particularly preferably, the temperature T is 90° C.

The corresponding step of the prior art process has two parts:
(i) acylation with ethylchloroformate at 0° C. and
(ii) ring closure at reflux (90° C.).

HPLC analysis of the products of the prior art process has shown that during the acylation mainly one intermediate is formed while the starting material disappears completely. Upon heating, however, a second, new, Intermediate is formed quickly, which slowly goes over to the desired 6-Cl-carsalam, together with some starting material. The first intermediate is the N-acylated salicylamide (X), and the second is the O-acylated derivative (XX) (via the phenolic OH).

In order to overcome the environmental problems associated with the prior art process, the inventors of the present invention first looked at an aqueous system, using a base such as sodium hydroxide instead of pyridine. However, it was found that when running the reaction in an aqueous medium with, for example, sodium hydroxide or sodium carbonate instead of pyridine, after ring closure and the formation of compound IIA, much more starting material IA was present than in the prior art process suggesting that the reaction had not gone to completion or that decomposition had occurred.

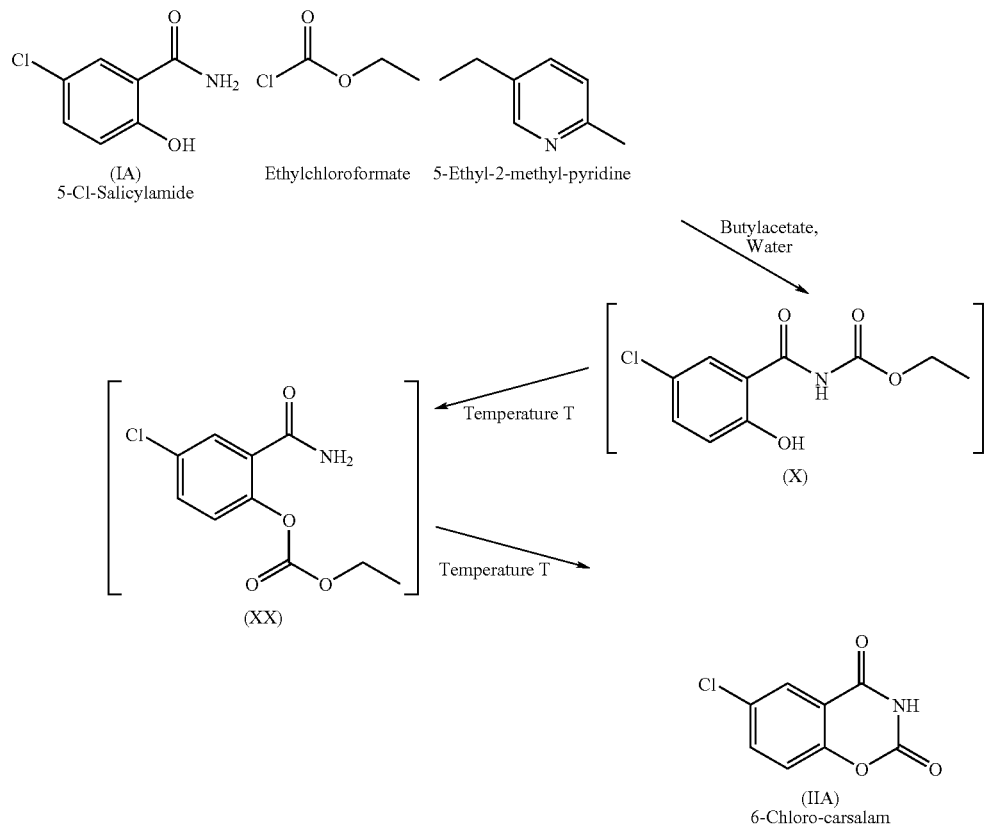

Scheme 5

A notable weakness of the prior art process is that it mainly gives a product which contains up to 10% of the starting amide (IA). A second weakness is that the process is run in acetonitrile and pyridine (as can be seen from Scheme 1), where both acetonitrile and pyridine are unsuitable for recycling. This is both commercially more costly and environmentally less desirable.

It was hypothesized that a further intermediate product is therefore formed, which upon heating may revert back to the starting material. This could be the O-acylated amide, which is not separated by HPLC. This may be consistent with an increased reactivity at the amide-oxygen atom, as it is usually the case with strong bases, which favour O-acylation.

Another explanation could be the decomposition of 6-chlorcarsalam under basic conditions in the same manner as occurs in Step B (ring opening with sodium carbonate at elevated temperature in dimethylformamide). However this explanation does not apply with pyridine. It was apparent, therefore, that mild organic bases were much to be preferred.

In order to overcome the aforementioned "incomplete" reaction problem, the present invention provides a two-phase system. A preferred system is alkylacetate/organic base/water, for example butylacetate/substituted-pyridine/water, with an excess ethylchloroformate. Most preferred is n-butyl acetate/5-ethyl-2-methyl pyridine/water.

It is hypothesized that in presence of water, hydrolysis of any unwanted intermediates (for example the O-acylated intermediate) occurs rapidly, allowing acylation at the desired N atom (an amide nitrogen) so long as there is enough chloroformate. Under these conditions (20% excess ethylchloroformate and 30% alkyl-substituted pyridine) only 1-2% starting material is found after ring closure.

Since pyridine is not easily recovered from the aqueous mother liquors it is preferably replaced, without loss of selectivity, with a non-water soluble pyridine derivative, especially an alkyl pyridine, for example the non-water soluble 5-ethyl-2-methyl-pyridine. The use of a non-water soluble alkyl-pyridine allows the base to be recovered and so is preferred.

The organic acetate solvent may be selected from methyl acetate, ethyl acetate, n-propyl acetate, isopropyl acetate or n-butylacetate. The preferred solvent is n-butylacetate, which azeotrope boils at about 90° C. This allows a fast reaction typically of about 4-5 h at reflux. The reaction in other solvents, such as ethyl acetate or isopropyl acetate although successful, requires more time since the boiling points of these solvents are lower.

Butylacetate is further preferred due to its low aqueous solubility characteristics. Since butylacetate is substantially insoluble with water, it keeps IA in solution, thus yielding a very pure product (higher than 98%). This is purer than the prior art process in which a less pure product of a mixture of IA/IIA is given. The yield of the reaction is over 90%, which is similar to the prior art process, except that the higher purity of the present process means that the overall yield of the product IIA is higher for the present invention.

During ring closure, the mixture is preferably slowly (within two hours) heated from 0° C. through to about 90° C. and refluxed.

It is noted that in the process of the present invention, no over-alkylated carsalam (which could be formed when IIA reacts with ethylchloroformate) was observed, thus showing that excess reagent is destroyed before ring closure occurs, which is beneficial.

IIA is readily purified by refluxing it in ethyl acetate/water allowing removal of up to 10% starting material without loss of yield, should this be necessary.

By-Products of Step A

The corresponding 3,5-dichloro-isomer may be present in the starting material IA, leading to the 3,5-dichloro-isomer by-product. Preferably less than 1% and in particular less than 0.5% of the 3,5-dichloro-isomer is present in either the starting material or the final product, more preferably less than 0.07%

Step B

Reference is made in particular to Scheme 6 below:

The compound ethyl-8-bromo-octanoate (EBO), which is used in the prior art processes comes at a high cost, both financially and environmentally since not only is it relatively expensive to buy but also, due to its high reactivity, It is a potential mutagenic alkylating agent and so causes serious safety issues both for its use and its disposal. On the other hand, the chloro equivalent, ECO, is cheaper and, due to its lower reactivity, is less of an environmental problem and health hazard. The health, economic and environmental advantages of ECO therefore enhance the benefits of the process of the present invention.

In the development of the process of the invention, the change from EBO to ECO initially posed significant problems during this alkylation/deprotection step, which results in the free acid (IV.II) or (IVA). These problems were however identified and overcome, as will be seen below, to establish the method of the present invention.

Scheme 6

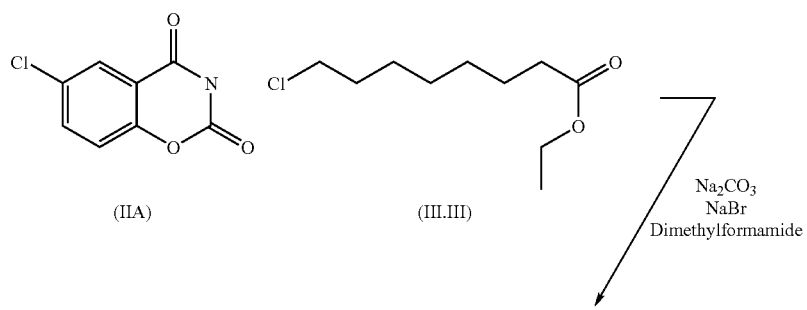

(IIA)　　　(III.III)

Na$_2$CO$_3$
NaBr
Dimethylformamide

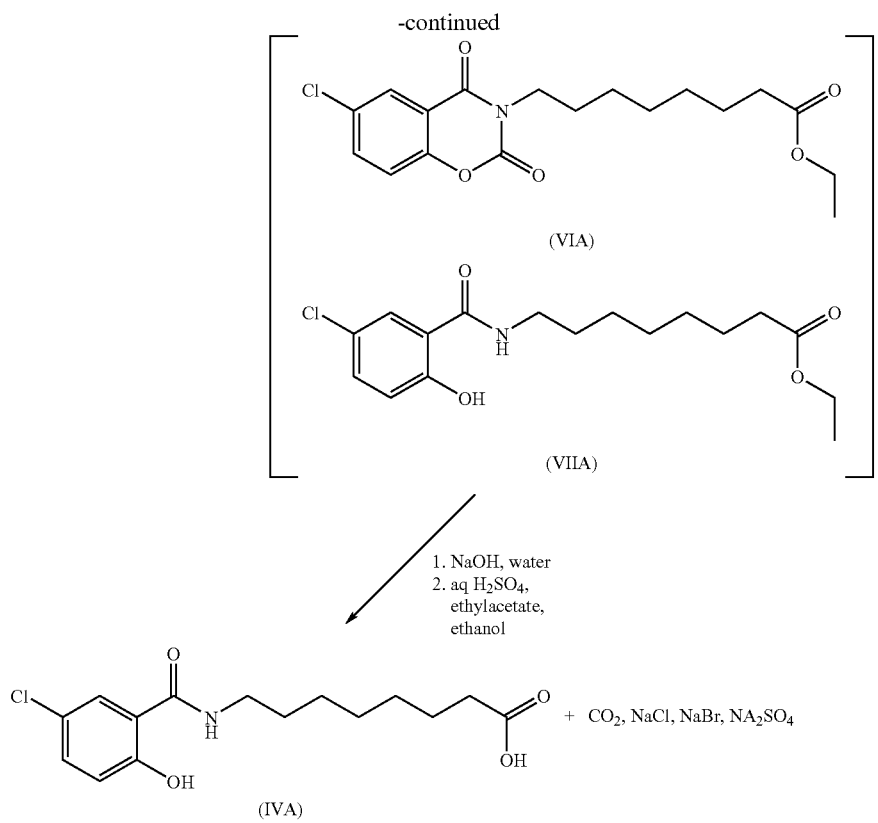

It was found that compared to prior art, alkylation with only ECO present was slow at 80° C., presumably due to the lower reactivity of the chlorine-reagent. Further, with prolonged reaction time (required to ensure completion) more side products were formed. For example, under the same conditions 0.1% di-acid by-product was formed with EBO, and 7% with ECO.

Increasing the temperature to 100° C. increased the rate of the reaction but also increased the rate of decomposition of the "carsalam" salt. In fact in presence of moisture, sodium carbonate does not give cleanly the carsalam-sodium salt, it also opens partially the ring, producing the corresponding amide (IA) which reacts at both positions O and N. The di-alkylated by-product which is thereby formed is not easily removed in the final step and therefore contaminates the final product. Formation of the di-alkylayed product is therefore not desirable.

From experiments it was noted that only 2.2% di-acid byproduct was generated with 1 eq. NaBr at 80° C. in comparison to 7% without NaBr.

Under the preferred, optimized, conditions of 1 equivalents ECO, 0.2 equivalents sodium bromide, 0.55 equivalents sodium carbonate, at 100° C., the alkylation proceeds with 95% selectivity accompanied by only about 2% di-alkylation, less than 1% O-alkylation and full consumption of ECO.

Finally, in order to prevent degradation of (IIA), in the laboratory scale synthesis, the base (typically sodium carbonate) and IIA are preferably first mixed together in an aprotic solvent (preferably dimethylormamide), and heated to 100° C. prior to a slow addition of (III.III). With exemplary amounts being 0.98 equivalents of (III.III), 0.6 equivalents base (typically sodium carbonate) and 0.1 equivalents of sodium bromide, the present invention provides, reproducibly, an alkylation with about 95% desired product (mixture of ring closed and opened ester), about 2% di-alkylated ester and about 3% remaining (IIA).

It was found that, where sodium carbonate is used as the base, mixing all the starting materials together at room temperature followed by heating at a given rate led to the uncontrolled release of $CO_2$, together with a transient thickness of the slurry, which is not convenient.

Therefore, in an enhanced synthesis, all of the starting materials except sodium carbonate are mixed together. The resulting mixture is then heated up to 100° C. and only then is the sodium carbonated slowly added, preferably portionwise, or continuously in the solid form. No reaction occurs without sodium carbonate. The sole parameters to control are the amount and rate of base (sodium carbonate) addition.

For this alternative variation of the synthesis of the present invention, a slight excess of sodium carbonate is preferred (0.55 equivalents which corresponds to 1.05-1.1 equivalents base) and preferably the sodium carbonate is added over about 2 hours. This gives a reaction with only a minor side reaction (less than 1% di-alkylation). In order to obtain more than 95% selectivity (i.e. 95% of the desired conversion), 1 equivalents of (III.III) (instead of 0.98) and 0.2 equivalents sodium bromide (instead of 0.1 equivalents) are advantageously used.

Ring opening occurs by the end of the reaction of step B1, although this tends not to be complete and is believed to be dependent on the amount of excess of sodium carbonate used. Typically at least 30-50% ring opening occurs by the end of the reaction step, making the isolation of the pure intermediate (VIA) undesirable. Advantageously, however, saponification and completion of the ring opening are then carried out immediately in the same vessel since after saponification both intermediates (VIA and VIIA) give the desired product, IVA. Thereby one single product IVA (5-CNAC free acid) is obtained, which can be isolated after acidification.

To optimise the saponification, so avoiding isolation of the intermediate, preferably the solvent should be eliminated totally by distillation. In order to do this, it is preferred to use dimethylformamide instead of dimethylacetamide, since DMF has a lower boiling point.

The solvent is removed by distillation under vacuum at 100° C., leaving an oily heterogeneous residue. The latter was mixed with water and treated at 80-100° C. with excess sodium hydroxide. Ring opening and saponification are very rapid. After saponification, the solution was cooled to 60° C., neutralized with sulfuric acid to pH 8-9 and afterwards diluted with ethylacetate.

Thereafter, the pH was lowered to 2-3, allowing the product to go into the organic phase. The water phase is discarded and the organic phase is washed with water. Then fresh water was added and the ethylacetate distilled off under normal pressure, leaving IVA as a suspension in water. At that stage, or even before, isolation of the crude product is possible.

The aqueous suspension was diluted with ethanol, which allowed the dissolution of the acid (IVA) at around 60° C. To this solution is added an amount of sodium hydroxide, which was revealed to be necessary to keep the di-acid by-product in the solution (and thus not contaminate the crystallisation process). Upon cooling pure IVA crystallizes out of the solution. It is collected by centrifugation at 0° C. and dried under vacuum at 60° C. Preferably, the di-acid is present below 0.6%.

The above crystallization of IVA is optimized in such a way to remove the by-products (mainly remaining starting material, di-acid and in some cases the dimer). Preferably the final product, IVA, is greater than 99% pure with less than 0.2% of the dimer present.

By-Products of Step B (III.III) (ethyl-8-chlorooctanoate).

Preferably, the ethyl-8-chlorooctanoate does not contain any dichlorohexane. It has been shown that in a sample containing up to 1% dichlorohexane plus other by-product, the dichlorohexane reacts with IIA to form a dimeric by-product, which is, as has be mentioned before, extremely difficult to separate out form the final acid product (IVA). Particularly preferably, ethyl-8-chlorooctanoate at >99% purity with less than 0.1% dichlorohexane is used.

Where sodium carbonate is used it must be highly pure since impure compound can lead to incomplete reaction, extended ring opening and excessive di-alkylated by-product formation.

A possible by-product is the 5-CNAC ethylester, which may be formed due to incomplete saponification or formed by esterification of the free acid during the end crystallization from ethanol/water.

Further, as indicated earlier, there may be residual IA, the corresponding 5-chlorosalicylic acid and the so-called "dimer" if more then 0.1% dichlorhexane is present in (III.III).

With 0.1% dichlorohexane in (III.III) it is predicted that the dimer contamination could be about 0.3% in IVA and below 0.1% in (VA).

In order to further purify (IVA), if required, an additional extraction with butylacetate after the saponification and partial neutralization may be conducted. At that stage, at pH 8-9. IVA is still water soluble (as its mono sodium salt) whereas the dimer, which cannot make a salt at this pH (no carboxylic acid), may be extracted. The main drawback of this modification is that a large amount of butylacetate is necessary to obtain a phase separation.

Other potential impurities like chlorine isomers in the aromatic ring and C7, C8 homologues of the alkyl chain may theoretically be present in small quantities (less than 0.05%) but preferably are already excluded due to their control in the starting materials.

In order to keep by-products to the minimum, it is preferred that, in particular, the following parameters are regulated, as hereinbefore described:

Quality and amounts of starting materials: (IIA), (III.III), base (such as sodium carbonate), bromine salt (such as sodium bromide).

Temperature of the reaction mixture and rate of sodium carbonate addition.

Distillation of the aprotic solvent (such as DMF), and amount of strong base (e.g. sodium hydroxide) (saponification).

Ratio ethanol/water and amount sodium hydroxide during crystallization.

Furthermore, the quality and relative amounts of starting materials are important for the quality of (IVA). Too much (III.III) and sodium carbonate (or too little IIA) is likely to have a direct impact on the amount of di-alkylated by-product formed, which to a certain extent is removed on the crystallization and potential rework. However a drop in the yield may also play a role in the formation of by-products, for example for about 20% less yield 10% over alkylation has been observed.

The present invention has therefore revised and improved the process of the prior art, and provided a "one pot" process to enable an increase the yield by as much as 20 percentage points (about 84% versus 64%) with equal or better purity.

Step C

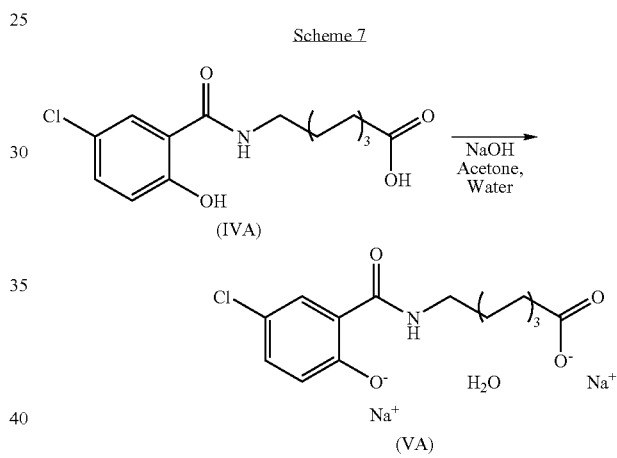

The prior art crystallization techniques had the following disadvantages: Crystallization occurred under reflux from an emulsion (after addition of concentrated sodium hydroxide to 5-CNAC free acid in acetone) without seeding. Therefore, no control of the crystallization was possible, although it might be that a certain thermodynamic equilibrium is obtained under these crystallization conditions, preventing such a control.

The present invention has provided a crystallisation technique in which the N-substituted salicylcamide (IV, IV.II and IVA) crystallises in an acetone/water mixture in the presence of an alkali metal base, especially sodium hydroxide. Independent from the reaction conditions, a polyhydrate, for example a hexahydrate, of IV, IV.II or IVA crystallizes first in the acetone/water mix, which then forms the monohydrate V or VA upon drying. Usually the wet cake contains about 12% water which is consistent with 2-3 molecules of water per 5-CNAC molecule.

Crystallization with only one equivalent water may be achieved using sodium methylate. This may give a solvate which corresponds to a different crystal modification.

Step C is itself inventive. In the preferred method steps, compound (IV.II or IVA), acetone and water are combined. The acetone:water ratio may be from about 5:1 v/v to about 15:1 v/v, e.g. about 10:1 to 11:1. A base is added to the mixture suitably at a slightly elevated temperature, e.g. about 40° C. to 60° C., for example 45° C. to 55° C. Further acetone may be added, for example as an acetone/water mixture, (e.g. from 2:1 v/v to 4:1 v/v, such as 3:1 v/v), suitably keeping the temperature at a moderately elevated level (e.g. 45° C.-55° C.). The salt is then isolated. One procedure is as follows: if the temperature is above 50° C., it is reduced to 50° C. or less (e.g. 40° C. to 50° C. such as 45° C. to 48° C.) and seed crystals are added to induce crystallisation, before further reducing the temperature (e.g. to 0° C. to 5° C.) to finish the crystallisation step prior to isolating the crystals. Stirring is suitably continued throughout. The crystals may be dried under vacuum 50-60 mbar at 50-55° C. for at least 24 hours.

It was observed that crystallization and stirring which occurred at higher temperatures (40-50° C.), afforded larger crystals (up to 500 micron). Further, crystallisation at about 0° C. provides different crystal types to those at higher temperatures.

In an alternative crystallisation process, the crystallisation is conducted from 2-pentanone at 80° C.

Preferably, crystallisation occurs, with seeding, at 45-50° C., followed by the addition of more acetone at the same temperature, then cooling to 0° C. to give the desired polymorph. A particularly favourable polymorph is obtained by prolonged stirring over 24 h at 0° C.

The resulting salt, V or VA is preferably >99% pure, without any by-product over 0.1%.

The theoretical amount of water in VA should be 4.8% calculated for a monohydrate. In fact the water content depends of the conditions and duration of drying. At 80-100-mbar pressure and 40-55° C. no over-drying occurs. However to avoid any risk it is recommended to check the water content during the drying process. Further, it appeared in some cases that the residual amount of acetone after drying was over the established limit of 0.5%.

In order to keep by-products to the minimum, it is preferred that, in particular, the following parameters are regulated, as hereinbefore described:

The amount and quality of the alkali metal base (sodium hydroxide)
The temperature of seeding and crystallization
The rate of saturation
The rate of cooling
The time of agitation at 0° C.
The drying procedure.

Throughout the description and claims of this specification, the words "comprise" and "contain" and variations of the words, for example "comprising" and "comprises", means "including but not limited to", and is not intended to (and does not) exclude other moieties, additives, components, integers or steps.

In the processes of the present invention, it is contemplated that wherever desired, one or more protecting groups may be present in the compounds for one or more of the functional groups that are not to participate in a particular reaction or reaction step or stage, or that would interfere with the reaction.

The protection of functional groups by such protecting groups, suitable reagents for their introduction, suitable protecting groups and reactions for their removal will be familiar to the person skilled in the art. Examples of suitable protecting groups can be found in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974.

Suitable hydroxy-protecting groups are especially selected from those of the acryl or ester type, e.g. lower alkanoyl, such as formyl, acetyl or isobutyroyl, benzoylformyl, chloroacetyl, dichloroacetyl, trichloroacetyl, trifluoroacetyl, methoxyacetyl, phenoxyacetyl, phenylacetyl, p-phenylacetyl, diphenylacetyl, 2,6-dichloro-4-methylphenox-yacetyl, 2,6-dichloro-4-(1,1,3,3-tetramethylbutyl)phenoxyacetyl, 2,4-bis (1,1-dimethylpropyl)phenoxyacetyl, chlorodiphenyl-acetyl, 3-phenylpropionyl, 4-azidobutyroyl, 4-methylthiomethoxybutyroyl, (E)-2-methyl-2-butenoyl, 4-nitro-4-methylpentanoyl, 4-pentenoyl, 4-oxopentanoyl, 4,4-(ethylenedithio)-pentanoyl, 5-[3-bis(4-methoxyphenyl)-hydroxymethylphenoxy)laevulinyl, pivaloyl, crotonoyl, monosuccinoyl, benzoyl, p-phenylbenzoyl, 2,4,6-trimethylbenzoyl, 2-(methylthiomethoxy-me-thyl)benzoyl, 2-(chloroacetoxymethyl)benzoyl, 2-[(2-chloroacetoxy)ethyl]benzoyl, 2-[(2-benzyloxy)ethyl]benzoyl, 2-[2-(4-methoxybenzyloxy)ethyl]benzo-yl, 2-iodobenzoyl, o-(dibromomethyl)benzoyl, o-(methoxycarbonyl)benzoyl, 2-chlorobenzoyl, 4-bromobenzoyl, 4-nitrobenzoyl, alkoxycarbonyl, such as methoxycarbonyl, ethoxycarbonyl, isobutoxycarbonyl, methoxymethylcarbonyl, 9-fluorenylmethoxycarbonyl, 2,2,2-trichloroethoxycarbonyl, 1,1-dimethyl-2,2,2-trichloroethoxycarbonyl-, 2-(trimethylsilyl) ethoxycarbonyl, 2-(phenylsulfonyl)-ethoxycarbonyl, 2-(triphenylphosphonio)ethoxycarbonyl, vinyloxycarbonyl, allyloxycarbonyl, p-nitrophenoxycarbonyl, benzyloxycarbonyl, p-methoxybenzyloxycarbonyl, 3,4-dimethoxy-benzyloxycarbonyl, o-nitrobenzyloxycarbonyl, p-nitrobenzyloxycarbonyl, dansylethoxy-carbonyl, 2-(4-nitrophenyl) ethoxycarbonyl, 2-(2,4-dinitrophenyl)ethoxycarbonyl, 2-cyano-1-phenylethoxycarbonyl, S-benzylthlocarbonyl, 4-ethoxy-1-naphthyloxycarbonyl, 3',5'-di-methoxybenzoinyloxycarbonyl, 2-methylthiomethoxyethoxycarbonyl, N-phenylcarbamoyl, dimethylethylphosphinothiolyl, methyldithiocarbonyl; N,N,N',N'-tetr'amethylphosphoro-diamidoyl, sulfonyl, methanesulfonyl, benzenesulfonyl, toluenesulfonyl, 2-[(4-nitrophenyl)-ethyl]sulfonyl, allylsulfonyl, 2-formylbenzenesulfonyl, nitroxy, or protecting groups of the ether type, such as methyl, substituted methyl, preferably lower alkoxymethyl, especially methoxymethyl (MOM), methylthiomethyl, (phenyldimethylsilyl)methoxymethyl, benzyloxy-methyl, p-methoxybenzyloxymethyl, p-nitrobenzyloxymethyl, guaiacolmethyl, tert-butoxy-methyl, 4-pentenyloxymethyl, silyloxymethyl, lower alkoxy-lower alkoxymethyl, especially 2-methoxyethoxymethyl (MEM), 2,2,2-trichloroethoxymethyl, 2-(trimethylsilyl)-ethoxymethyl or menthoxymethyl, tetrahydropyranyl, 3-bromotetrahydropyranyl, tetrahydrothiopyranyl, 4-methoxythiopyranyl, 1-methoxycyclohexyl, 4-methoxytetrahydrothiopyranyl, S,S-dioxy-4-methoxytetrahydrothiopyranyl, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothio-furanyl, 2,3,3a,4,5,6,7,7a-octahydro-7,-8,8-trimethyl-4,7-methanobenzofuran-2-yl; substituted ethyl, such as 1-ethoxyethyl, 1-(2-chloroethoxy)ethyl, 1-[2-(trimethylsilyl)ethoxy]ethyl-, 1-methyl-1-methyl-i-benzyloxyethyl, 1-methyl-1-benzyloxy-2-fluoroethyl-1,1-methyl-1-phenoxyethyl, 2,2,2-trichloroethyl, 1,1-dianisyl-2,2,2-trich-loroethyl, 1,1,1,3,3,3-hexafluoro-2-phenylisopropyl, 2-trimethylsilylethyl, 2-(benzylthio)ethyl, 2-(phenylselenyl) ethyl, tert-butyl; allyl or propargyl, substituted phenyl ethers, such as p-chlorophenyl, p-methoxyphenyl, p-nitrophenyl, 2,4-dinitrophenyl or 2,3,5,6-tetrafluoro-4-(trifluoromethyl)-phenyl, benzyl, substituted benzyl, such as p-methoxybenzyl, 3,4-dimethoxybenzyl, o-nitrobenzyl, p-nitrobenzyl, p-halobenzyl, e.g. p-bromobenzyl, 2,6-dichlorobenzyl, p-cyanobenzyl, p-phenylbenzyl, 2,6-difluorobenzyl, p-azidobenzyl, 4-azido-3-chlorobenzyl, 2-tri-fluoromethylbenzyl or p-(methylsulfinyl)benzyl, 2- or 4-picolyl, 3-methyl-2-picolyl, 2-quin-olinylmethyl, 1-pyrenylmethyl, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxy-phenyl)phenylmethyl, tri(p-methoxyphenyl)methyl, 4-(4'-bromophenacyloxy)phenyl-diphenylmethyl, 4,4',4'-tris(4,5-dichloroph-thalimidophenyl)methyl), 4,4',4'-tris(laevulinoyl-oxyphenyl)methyl, 4,4',4'-tris(benzoyloxyphenyl)methyl, 4,4'-dimethoxy-3"-[N-(imidazolylme-thyl)]trityl, 4,4'dimethoxy-3"-[N-(imidazolylethyl)carbamoyl]trityl, 1,1-bis(4-methoxy-phenyl)-1'-pyrenylmethyl, 4-(17-tetrahydrobenzo[a,c,g,f-luorenylmethyl)-4',4"-dimethoxytrityl, 9-anthryl, 9-(9-phenyl)xanthenyl, 9-(9-phenyl-10-oxo)anthryl, 1,3-benzodithiolan-2-yl, S,S-diox of the silyl ether type, such as tri-lower alkylsilyl, e.g. trimethylsilyl, triethylsilyl, triisopropylsilyl, dimethylisopropylsilyl, diethylisopropylsilyl, dimethylthexylsilyl, tert-butyldimethylsilyl or di-tert-butylmethylsilyl, tert-butyldiphenylsilyl, triphenylsilyl, diphenylmethylsilyl, tris(trimethylsilyl)silyl, (2-hydroxystyryl)dimethyl-silyl, (2-hydroxystyryl)-diisopropylsilyl, tert-butylmethoxyphenylsilyl or tert-butoxydiphenylsilyl.

Carboxy-protecting groups are especially ester-forming, enzymatically and/or chemically removable protecting groups, preferably enzymatically and/or chemically removable protecting groups, such as heptyl, 2-N-(morpholino) ethyl, cholinyl, methoxyethoxyethyl or methoxyethyl; or those which are primarily chemically removable, e.g. alkyl, such as lower alkyl, especially methyl, ethyl, substituted lower alkyl (except for benzyl and substituted benzyl), such as substituted methyl, especially 9-fluorenylmethyl, methoxymethyl, methoxy-ethoxymethyl, methylthiomethyl, 2-(trimethylsilyl)ethoxymethyl, benzyloxymethyl, pivaloyloxy-methyl, phenylacetoxymethyl, triisopropylsilylmethyl, 1,3-dithianyl-2-methyl, dicyclopropyl-methyl, acetonyl, phenyl, p-bromophenacyl, a-methylphenacyl, p-methoxyphenacyl, desyl, carbamidomethyl, p-azobenzenecarboxamidomethyl, N-phthalimidomethyl or 4-picolyl, 2-substituted ethyl, especially 2-iodo-, 2-bromo- or 2-chloro-ethyl, 2,2,2-trichloroethyl, 2-(trimethylsilyl)ethyl, 2-methylthioethyl, 2-(p-nitrophenylsulfenyl)ethyl-1,2-(p-toluenesulfonyl)-ethyl, 2-(2'-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl or 2-cyanoethyl, tert-butyl, 3-methyl-3-pentyl, 2,4-dimethyl-3- or .omega.-chloro-lower alkyl, especially 4-chlorobutyl or 5-chloropentyl, cyclopentyl, cyclohexyl, lower alkenyl, especially allyl, methallyl, 2-methylbut-3-en-2-yl, 3-methylbut-2-enyl or 3-buten-1-yl, substituted lower alkenyl, especially 4-(trimethylsilyl)-2-buten-1-yl, cinnamyl or a-methylcinnamyl, lower alkynyl, such as prop-2-ynyl, phenyl, substituted phenyl, especially 2,6-dialkylphenyl, such as 2,6-dimethylphenyl, 2,6-diisopropylphenyl, 2,6-di-tert-butyl-4-methylphenyl, 2,6-di-tert-butyl-4-methoxyphenyl, p-(methylthio)-phenyl or pentafluorophenyl, benzyl, substituted benzyl, especially triphenylmethyl, diphenyl-methyl, bis(o-nitrophenyl)methyl, 9-anthrylmethyl, 2-(9,10-dioxo)anthrylmethyl, 5-dibenzo-suberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, 4-azidomethoxybenzyl, 4-(N-[1-(4,4-dimethyl-2,6-dioxocycl-ohexylidene)-3-methylbutyl]amino)benzyl, piperonyl or p-polymer-benzyl, tetrahydro-pyranyl, tetrahydrofuranyl, or silyl radicals, such as tri-lower alkylsilyl, especially trimethylsilyl, triethylsilyl, tert-butyldimethylsilyl, isopropyldimethylsilyl or di-tert-butylmethylsilyl, or phenyl-di-lower alkylsilyl, such as phenyldimethylsilyl; alternatively a carboxy group can also be protected in the form an oxazolyl, 2-alkyl-1,3-oxazolinyl, 4-alkyl-5-oxo-1,3-oxazol-idinyl or 2,2-bistrifluo 4-alkyl-5-oxo-1,3-oxazolidinyl radical.

Amide-protecting groups are especially allyl, tert-butyl, N-methoxy, N-benzoyloxy, N-methyl-thio, triphenylmethylthio, tert-butyldimethylsilyl, triisopropylsilyl, 4-(methoxymethoxy)phenyl, 2-methoxy-1-naphthyl, 9-fluorenyl, tert-butoxycarbonyl, N-benzyloxycarbonyl, N-methoxy- or N-ethoxy-carbonyl, toluenesulfonyl, N-buten-1-yl, 2-methoxycarbonylvinyl, or especially alkyl, such as lower alkyl, or more especially substituted alkyl, especially benzyl, benzyl substituted by one or more radicals selected from lower alkoxy, such as methoxy, lower alkanoyloxy, such as acetoxy, lower alkylsulfinyl, such as methylsulfinyl, dicyclopropylmethyl, methoxymethyl, methylthiomethyl and N-benzoyloxymethyl; or bis(trimethylsilyl)methyl, trichloroethoxymethyl, tert-butyldimethylsilyloxymethyl, pivaloyloxymethyl, cyanomethyl, benzyl, 4-methoxybenzyl, 2,4-dimethoxybenzyl, 3,4-dimethoxybenzyl, 2-acetoxy-4-methoxy-benzyl, o-nitrobenzyl, bis(4-5 methoxyphenyl)phenylmeth-yl, bis(4-methylsulfinylphenyl)methyl, pyrrolidinomethyl, diethoxymethyl, 1-methoxy-2,2-dimethylpropyl or 2-(4-methylsulfonyl)ethyl.

It is characteristic of protecting groups that they are simple to remove (that is to say without undesirable secondary reactions taking place), for example by solvolysis, reduction, photolysis or alternatively under conditions analogous to physiological conditions, for example enzymatically. Typically, the protecting and activating steps are performed simultaneously.

The process of the present invention will now be further described in the following examples for the synthesis of 5-CNAC:

EXAMPLES

Example 1

Preparation of 6-chloro-2H-1,3-benzoxazine-2,4(3H)-dione

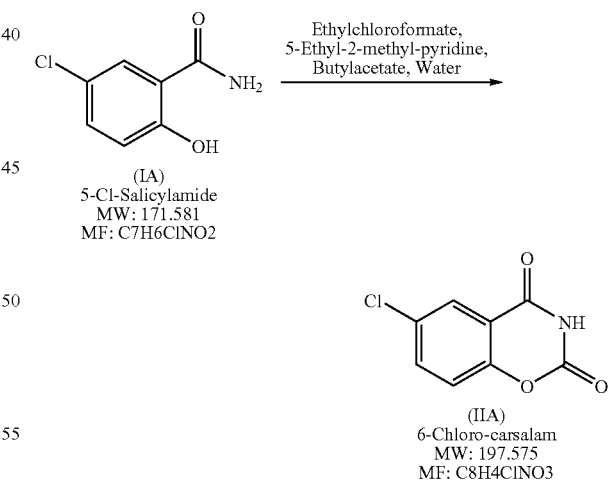

5-chlorosalicylamide (300 g, 1.75 mol) and water (900 ml) were placed in a 3 liter, 4-neck round-bottomed flask under a nitrogen atmosphere and stirred. 5-ethyl-2-methyl-pyridine (284 g, 2.27 mol) and n-butyl acetate (900 ml) were added to the mixture. The mixture was cooled to 0-5° C. (jacket-10° C.) and dropwise addition of ethyl chloroformate (233 g, 2.10 mol) was started. This addition continued over a period of approximately one hour. When the addition was completed, the reaction mixture was slowly heated (in about two hours) to reflux and kept under reflux for an additional period of about 5 hours (jacket 110° C., internal temperature (IT) 90° C.). The resulting slurry was allowed to cool to room temperature, and hydrochloric acid (28 ml, 37% m/m, 0.34 mol) was added and the mixture stirred for about 30 minutes. The resulting slurry was vacuum filtered, the filter cake was washed with n-butyl acetate followed by water (600 ml) and was allowed to dry overnight in vacuo at 60° C. 321 g (93%) of 6-chloro-2H-1, 3-benzoxazine-2,4(3H)-dione (6-chloro carsalam) was isolated after drying.

Example 2

Preparation of N-5-(chlorosalicyloyl)-8-aminocaprylic acid (5-CNAC)

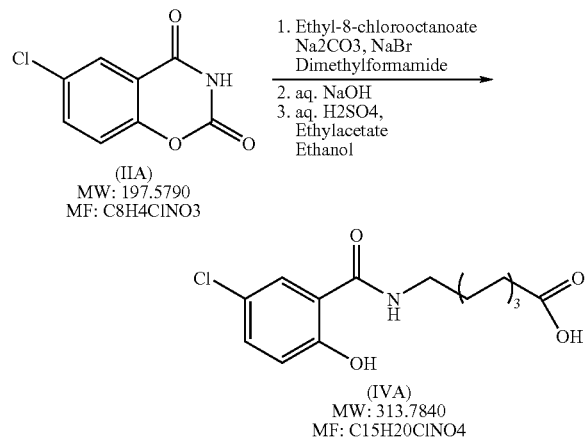

6-chloro-2H-1,3-benzoxazine-2,4(3H)dione (180.5 g, 0.91 mol), sodium bromide (18.7 g, 0.18 mol) and dimethylformamide (840 ml) were placed in a 3 liter, 4-neck round bottomed flask under a nitrogen atmosphere and stirred. Ethyl-8-chloro-octanoate (188.3 g, 0.911 mol) was added in one portion, and rinsed with dimethylformamide (60 ml). The mixture was heated up to 100-105° C. jacket 120° C.) and anhydrous sodium carbonate (51.7 g, 0.47 mol) was added portion wise over a period of 2 hours. After the reaction was complete, the solvent was distilled off under reduced pressure (60-20 mbar, internal temperature 75-120° C., jacket 100-130° C.) to leave an oily residue. Water (700 ml) was added at 85-95° C. over 10-20 minutes, followed by sodium hydroxide (380 ml, 30% w/w), followed by a rinse with 20 ml of water. The mixture was stirred for two hours at 85-100° C., then sulfuric acid (60 ml 50% w/w) was added at 60-65° C. until the pH of the mixture was between 8 and 9 then ethyl acetate (700 ml) was added at 60-65° C. over 30 to 60 minutes. Then more sulfuric acid (221 ml, 50% w/w) was added at 60-65° C. over a period of one hour until the pH of the mixture was between 2 and 3.5. Afterwards the two phases were allowed to separate. The aqueous phase was discarded, and the remaining organic phase washed with water (300-360 ml) at 60-65° C. Then water (600 ml) and sodium hydroxide (10.8 g, 30% w/w and 40 ml of water), followed by a rinse of 20 ml of water, were added (in order to remove small about of N,O-5-(chlorosalicyloyl)-di-octanoic acid by-product), and the organic solvent distilled off under atmospheric pressure (jacket 110-120° C., IT: 80-100° C.). To the resulting suspension, ethanol (1500 ml) was added at 50-65° C. The clear solution was allowed to cool down to 40-45° C. and seed crystals (0.12 g) were added and the solution stirred for 20 to 30 minutes until crystallisation was set on. Cooling was continued down to 0-5° C. in a period of 1-2 hours. The solid was collected by vacuum filtration and washed with ethanol/water 7:3 (540 ml), and dried under vacuum (10-50 mbar) at 60° C. overnight to yield 237 g of N-5-(chlorosalicyloyl)-8-aminocaprylic acid (84%).

Example 3

Preparation of the di-sodium salt, monohydrate of N-5-(chlorosalicyloyl)-8-aminocaprylic acid N-5-(chlorosalicyloyl)-8-aminocaprylic acid (3.5 kg, 11.15 mol), acetone (9450 ml) and water (875 ml, purified) were placed in a 50 liter vessel under a nitrogen atmosphere and stirred at 45-55° C. (jacket 60° C.) until a clear solution was formed (20 to 30 minutes). Sodium hydroxide (297 g, 30% w/w, 22.3 mol) was added in such a way as to maintain the temperature at 45-55° C., followed by a solution of acetone/water 3:1 v/v (1050 ml). The hot (50° C.) solution was passed then over a polishing filter and the filtrate transferred to another clean vessel and heated to 45 to 55° C. The transfer line was rinsed with hot (45-55° C.) acetone/water 3:1 v/v (1050 ml), and then acetone (about 10.5 liter) was added in such a way to keep the temperature around 45-55° C. (jacket 55° C.). Then, the temperature was lowered to 45-48° C. and seed crystals (4 g) were added. The mixture was stirred for about 20-30 minutes to obtain a fine suspension and induce crystallization, then more acetone (28 l) was added over one hour in such a way to maintain a temperature of 45-50° C. (jacket 55° C.). Afterwards, a slow stirring was prolonged for one hour at 45-50° C., then the temperature was lowered to 0-5° C. over a period of two hours. Stirring was continued at 0-5° C. for an hour, then crystals were collected by centrifugation, washed with cold acetone/water 95:5 v/v (7 l) and dried under vacuum 50-60 mbar at 50-55° C. for at least 24 hours to yield 4.19 kg of 5-CNAC di-sodium monohydrate (95% yield).

The invention claimed is:
1. In a method of preparing an N-substituted salicylamide, wherein the N-substituted salicylamide is achieved by reaction of a carsalam derivative with ethyl-8-bromooctoanoate, the improvement comprising: reacting the carsalam derivative with a chloro-substituted compound of formula (III)

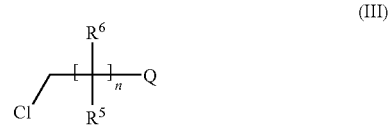

wherein n is an integer from 1 to 8, Q represents a group readily convertible to a carboxylic acid moiety and $R^5$ and $R^6$ are independently selected from hydrogen, —OH, $NR^3R^4$, halogen, $C_1$, $C_2$, $C_3$ or $C_4$ alkyl, $C_1$, $C_2$, $C_3$ or $C_4$ alkoxy, $C_2$, $C_3$ or $C_4$ alkenyl where $R^3$ and $R^4$ are each independently selected from hydrogen, —OH, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, $C_2$, $C_3$ or $C_4$ alkenyl,
wherein said reacting step is carried out by mixing in an inert atmosphere and in the presence of an aprotic solvent, the carsalam derivative with 1 equivalent of the chloro-substituted compound of formula III and 0.2 equivalents an alkali metal-bromide, heating to 100-105° C., followed by slow addition of 0.55 equivalents of an alkali metal hydroxide base or an alkali metal carbonate base.

2. A method according to claim 1 wherein the alkali metal-bromide enables the formation in situ of a compound of formula (IIIb)

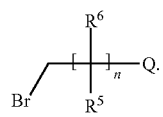

(IIIb)

3. A method according to claim 1 wherein the compound of formula (III) is a compound of formula (III.II):

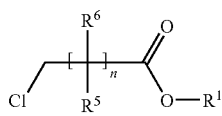

(III.II)

wherein $R^1$ represents a protecting group for the carboxylic moiety.

4. A method according to claim 3 wherein $R^1$ is selected from a linear or branched alkyl group containing 1, 2, 3, 4, 5 or 6 carbon atoms.

5. A method according to claim 4 wherein $R^1$ is ethyl.

6. A method according to claim 1 wherein n is 6.

7. A method according to claim 1 wherein each $R^5$ and $R^6$ represents H.

8. A method according to claim 1 wherein n is 6 and each $CR^5R^6$ is $CH_2$.

9. In a method of preparing a compound of the general formula IV:

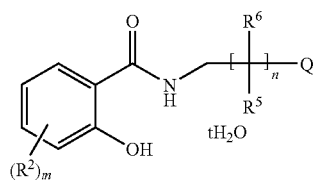

(IV)

where $R^5$, $R^6$, Q and n are as defined in claim 1, t is 0,1,2,3,4,5 or 6, m is 1,2,3 or 4 and $R^2$, or where m>1 each $R^2$ independently, is selected from —OH, $NR^3R^4$, halogen, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, $C_2$, $C_3$ or $C_4$ alkenyl and $R^3$ and $R^4$ are each independently selected from hydrogen, —OH, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, $C_2$, $C_3$ or $C_4$ alkenyl wherein the compound of formula IV is achieved by reaction of a carsalam derivative with ethyl-8-bromooctoanoate, the improvement comprising:

(i) reacting a compound of formula (I)

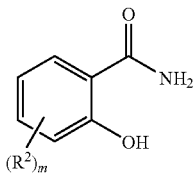

(I)

with a chloroformate in the presence of a weak organic base to form a compound of formula (II)

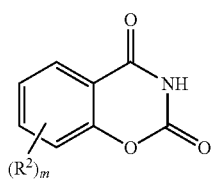

(II)

and (ii) reacting in an inert atmosphere and in the presence of an aprotic solvent, the compound of formula II with one equivalent of a compound of formula (III),

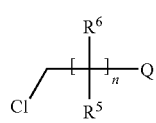

(III)

and 0.2 equivalents of an alkali metal-bromide, heating to about 100° C., followed by slow addition of 0.55 equivalents of an alkali metal hydroxide base or an alkali metal carbonate base to provide a compound of formula (IV).

10. A method according to claim 9 wherein the compound of formula (IV) is subjected to a subsequent saponification step.

11. A method according to claim 10 wherein the saponification step is carried out without prior isolation of the compound of formula (IV).

12. A method according to claim 9 wherein the compound of formula (IV) is formed in mixture with a compound of formula (VI)

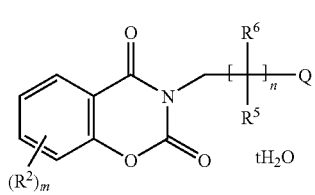

(VI)

where $R^2$, m, t, n and Q are as defined in claim 9.

13. A method according to claim 12 wherein the compounds of formulae (IV) and (VI) are subjected to a subsequent saponification step.

14. A method in according to claim 13 wherein the saponification step is carried out without prior isolation of the compounds of formulae (IV) and (VI).

15. A method according to claim 9 wherein compound (III) is a compound of the formula (III.II)

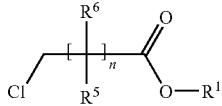
(III.II)

where $R^1$ is a protecting group for the carboxy moiety, whereby the compound of formula (IV) is a compound of the formula (IV.I):

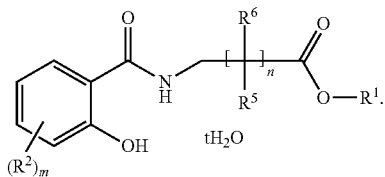
(IV.I)

16. A method according to claim 14 including the further step of removing the group $R^1$ to form a compound of the formula (IV.II):

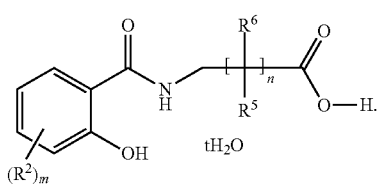
(IV.II)

17. A method according to claim 14 wherein the compound of formula (IV.I) is formed in mixture with a compound of formula (VI.I)

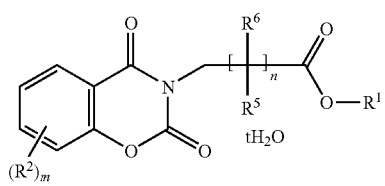
(VI.I)

where R2, m, t, n and Q are as defined in claim 9.

18. A method according to claim 16 including the further step of reacting the compounds of formulae (IV.I) and (VI.I) each to form a the compound of formula (IV.II).

19. A method according to claim 17 wherein said further step is performed without prior isolation of the compounds of formulae (IV.I) and (VI.I).

20. A method according to claim 17 wherein said further step comprises a saponification step.

21. A method according to claim 14 wherein $R^1$ is linear or branched alkyl containing 1, 2, 3, 4, 5 or 6 carbon atoms.

22. A method according to claim 20 wherein $R^1$ is ethyl.

23. A method according to claim 15, further comprising the additional step of reacting the compound of formula (IV.II) with $M_aY$ to provide the compound of formula (V):

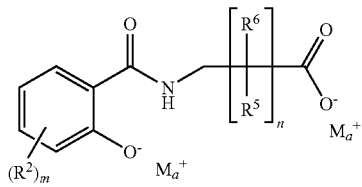
(V)

where $M_a$ is an alkali metal and Y is a basic counter ion.

24. A method according to claim 23, wherein the metal $M_a$ is Na.

25. A method according to claim 23, wherein Y is OH.

26. A method according to claim 23 wherein the compound (V) is a hydrate.

27. A method according to claim 23 wherein $M_aY$ is NaOH.

28. A method according to claim 9 wherein m is 1.

29. A method according to claim 9 wherein $R^2$ is chloro.

30. A method according to claim 27 wherein $R^2$ is at the 5-position.

31. A method according to claim 9 wherein every $R^5$ and every $R^6$ is hydrogen.

32. A method according to claim 9 wherein n is 6.

33. A method according to claim 9 wherein n is 6 and each $CR^5R^6$ is $CH_2$.

34. A method according to claim 15 wherein the compound of formula (IV.II) is N-(5-chlorosalicyloyl)-8-aminocaprylic acid.

35. A method according to claim 1, wherein the alkali metal bromide is NaBr.

36. A method according to claim 9 wherein the weak organic base is substantially water insoluble.

37. A method according to claim 9 wherein the weak organic base is an alkyl-substituted pyridine.

38. A method according to any claim 36 wherein the weak organic base is 5-ethyl-2-methyl-pyridine.

39. A method according to claim 9 wherein the chloroformate is ethylchloroformate.

40. A method according to claim 9 wherein step (i) is performed in the presence of an alkyl acetate.

41. A method according to claim 9, wherein step (i) is performed in a two phase system, the phases comprising respectively water and an organic solvent.

42. A method according to claim 41 wherein the organic solvent is an alkyl acetate.

43. A method according to claim 41 wherein the alkyl acetate is butyl acetate.

44. A method according to claim 23, wherein the additional step is performed in an acetone/water mix.

45. A method according to claim 44 wherein the acetone:water ratio is about 3:1.

46. A method according to claim 9 wherein the compound of formula (IV) contains less than 2.2% di-acid by-product.

47. A method according to claim 15 wherein the compound of formula (IV.II) contains less than 2.2% di-acid by-product.

48. A method according to claim 23 wherein the compound of formula (V) contains less than 2.2% di-acid by-product.

49. A method according to claim 16 wherein the compound of formula (IV.II) is the compound:

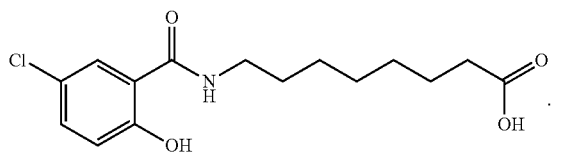
(IVA)

50. A method according to claim 23 wherein the compound of formula V is the compound:

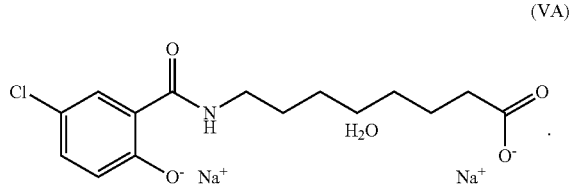 [SMILES: O=C([O-])CCCCCCCNC(=O)c1cc(Cl)ccc1[O-] ; [Na+] ; O ; [Na+]]
(VA)

51. A method according to claim 16 further comprising formulating a compound of formula (IV.II), into pharmaceutical formulation, the pharmaceutical formulation additionally having at least one active ingredient.

52. A method according to claim 49 further comprising formulating a compound of formula (IVA), into pharmaceutical formulation, the pharmaceutical formulation additionally having at least one active ingredient.

53. A method according to claim 23 further comprising formulating a compound of formula (V), into pharmaceutical formulation, the pharmaceutical formulation additionally having at least one active ingredient.

54. A method according to claim 50 further comprising formulating a compound of formula (VA), into pharmaceutical formulation, the pharmaceutical formulation additionally having at least one active ingredient.

55. A method according to claim 1 wherein the reaction mixture is heated to about 100° C.

56. A method according to claim 9 wherein the reaction mixture is heated to about 100° C.

* * * * *